United States Patent
Brandt et al.

(10) Patent No.: US 6,608,178 B1
(45) Date of Patent: Aug. 19, 2003

(54) 5-HYDROXYTRYPTOPHOL (5-HTOL) DERIVATIVES, ANTIBODIES, IMMUNOASSAYS AND DETECTION OF RECENT ALCOHOL CONSUMPTION

(75) Inventors: Ragnhild Brandt, Knivsta (SE); Olof Beck, Saltsjo-Boo (SE); Anders Helander, Uppsala (SE); Rose-Marie Jonsson, Uppsala (SE); Eric Unger, Uppsala (SE); Stefan Borg, Stocksund (SE); Eva Akerblom, Uppsala (SE)

(73) Assignee: Alco Dia A.B., Enebyberg (SE)

( * ) Notice: Subject to any disclaimer, the term of this patent is extended or adjusted under 35 U.S.C. 154(b) by 0 days.

(21) Appl. No.: 09/326,647

(22) Filed: Jun. 7, 1999

Related U.S. Application Data

(63) Continuation of application No. PCT/SE97/02035, filed on Dec. 5, 1997.

(30) Foreign Application Priority Data

Dec. 5, 1996 (SE) ............................................... 9604487

(51) Int. Cl.[7] ........................ C07K 16/44; G01N 33/53; G01N 33/84
(52) U.S. Cl. ............................ 530/387.1; 435/4; 435/7; 435/7.1; 435/7.21; 424/178.1; 424/130.1; 436/63; 436/89; 436/91; 436/96; 436/106; 436/111; 436/131; 436/161; 436/164; 436/166; 436/172; 436/174; 436/500; 422/52; 422/69; 422/70; 422/81; 422/82.05; 530/387.2
(58) Field of Search ........................ 435/4, 7, 7.1, 7.21; 424/178.1, 130.1; 436/63, 89, 91, 96, 106, 111, 131, 161, 164, 166, 172, 174, 500; 530/387.1, 387.2; 422/52, 69, 70, 81, 82.05

(56) References Cited

U.S. PATENT DOCUMENTS 4,762,781 A    8/1988  Geffard
5,824,559 A  * 10/1998  Nohta et al. ................ 436/111

FOREIGN PATENT DOCUMENTS

EP    0216162 A2     4/1987
EP    0216162 A   *  4/1987   ......... C07D/209/18
EP    0736770 A   * 10/1996   .......... G01N/33/68

OTHER PUBLICATIONS

Helander et al., 5–Hydroxytrytophol conjugates in man:Influence of alcohol consumption and altered serotonin turnover., Life sciences, vol. 56, No. 18, pp. 1529–1534, 1995.*
Helander et al., Determination of 5–hydroxytryptophol in urine by high–performance liquid chromatography: application of a new post–column derivatization method with fluorometric detection., Journal of Pharmaceutical & Biomedical Analysis, vol. 13, No. 4/5.*
Helander., Assay of urinary 5–hydroxytryptophol (5HTOL) detects relapse drinking during disulfiram therapy. Alcoholism Clinical and Experimental Research, 1997, vol. 21, No. 3. pp30A Abstract Only.*
Cheifetz et al., Occurrence and distribution of 5 hydroxy tryptophol in the rat., Journal of neurochemistry, 1980, vol. 34, No. 5, pp. 1093–1099. Abstract Only.*
Bobkova et al., Effect of induction of antibodies to serotonin on ethanol intake and brain mediatory systems in rats differing in alcoholic motivation., Patol. Fiziol. Eksp. Ter., 1989, 3, pp. 31–36, Abstract Only.*
Bobkova et al., Effect of active immunization of rats by conjugated serotonin–protein antigen on alcohol intake and content of biogenic amines in the brain and fluids., Patol. Fiziol. Eksp. Ter. 1988, 5, 25–29. Abstract Only.*
Tyce et al., Uptake and metabolism of 5–hydroxytryptamine by the isolated perfused rat liver., American journal of Physiology, 1968, vol. 215, No. 3, 611–619. Abstract Only.*
Manz et al., Radioimmunoassay of 5–hydroxy–3–indoleacetic acid., Journal of Clinical and Clinical Biochemistry., 1987, vol. 25, No. 2, pp. 101–106. Abstract Only.*
File WPI, Derwent accession No. 93–356458, Nat. Sci. Council; Monoclonal antibody mAbI2GiF12 to indole–3–acetic acid–obtd. from hybridoma cell I21F12, used for detection of indole–3–acetic acid, affinity chromatography and plant pathogenic mechanism studies; & JP, A, 5260989, 931012, DW9345. Abstract Only.
Henry Dabadie and Michel Geffard, "Identification of Tryptamine and Tryptamine–Serotonin Neurons in the Rat Dorsal Raphe Nuclei Using Specific Antibodies;" SYNAPSE, 1993, vol. 14, pp. 178–183.
Koichi Iijima et al.; "The distribution of serotonin immunoreactivity in the rat locus ceruleus after intraventricular injections of either 5,6– or 5,7–dihydroxytryptamine with special reference to serotonin synthesis;" ACTA HISTOCHEM, 1990, vol. 89, pp. 141–156.
D.J. Skene et al.; "Radioimmunoassay of pineal 5–methoxytryptophol in different species: comparison with pineal melatonin content," J. Endocr., 1986, vol. 110, pp. 177–184.
Anders Helander et al.; "5–hydroxytryptophol conjugation in man: influence of alcohol consumption and altered serotonin turnover," LIFE SCIENCES, 1995, vol. 56, No. 18, pp. 1529–1534.
T. Arndt et al.; "Labordiagnostik und Kontrolle des Alkoholabusus–ein Pladoyer fur Carbohydrate–Deficient–Transferrin (CDT)," Die Bedizinische Welt, 1994, vol. 45, pp. 247–257.

* cited by examiner

Primary Examiner—Christopher L. Chin
Assistant Examiner—Lisa V Cook
(74) Attorney, Agent, or Firm—Karen Lee Orzechowski; Liniak Berenato & White

(57) ABSTRACT

Antibody specific for a 5-HTOL compound. A glucuronide with 5-hydroxytryptophol (5-HTOL) characterized in that it comprises the structure of the β-glucuronide between the 5-hydroxy group of 5-HTOL and D-glucopyranosiduronic acid. An immunoassay and a diagnostic method utilizing the ummunoassay wherein a 5-hydroxytryptophol (5-HTOL) compound is determined by the use of an antibody specific for a 5-HTOL compound is used.

3 Claims, 2 Drawing Sheets

Figure 1:
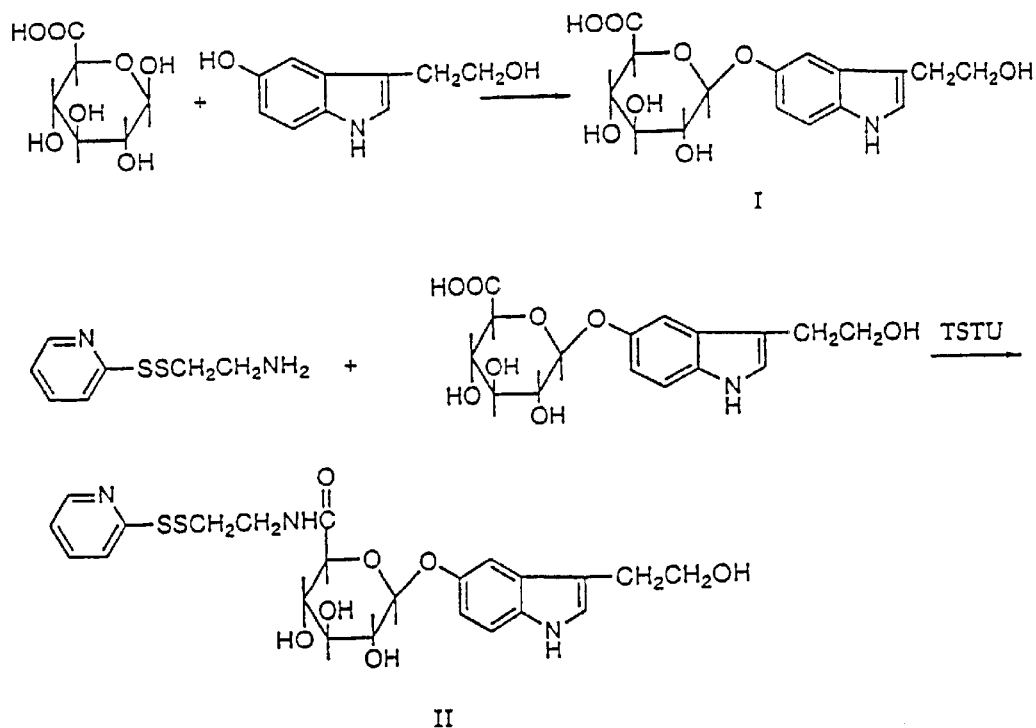

5-HYDROXYTRYPTOPHOL (5-HTOL) DERIVATIVES, ANTIBODIES, IMMUNOASSAYS AND DETECTION OF RECENT ALCOHOL CONSUMPTION

CROSS REFERENCES TO RELATED APPLICATIONS

This application is a continuation of the U.S. designation of International Application PCT/SE97/02035 filed Dec. 5, 1997.

TECHNICAL FIELD

The present invention concerns a novel antibody that may be used in immunoassays of components reflecting body fluid levels of 5-hydroxytryptophol [5-HTOL=2-(5-hydroxy-3-indolyl)ethyl alcohol]. Free 5-HTOL and glucuronide and sulphate conjugates thereof are known markers for recent alcohol intake in humans. Other aspects of the invention are as indicated in the title.

BACKGROUND ART 5-hydroxytryptophol (5-HTOL) and 5-hydroxyindole-3-acetic acid (5-HIAA) are human metabolites of serotonin (5-hydroxytryptamine, 5-HT) via the common intermediate 5-hydroxyindole-3-acetaldehyde (5-HIAL). 5-HTOL is excreted in the urine where it mainly occurs conjugated with a glucuronic acid (T-5-G (or GHTOL), 75–95%) and, to a lesser extent, in free form or conjugated as a sulphate. 5-HIAA is also excreted in the urine. After alcohol consumption, the 5-HTOL level in various body fluids will raise from normal values that for urine are in the range of 40–650 nmol/L. The 5-HTOL/5-HIAA ratio will simultaneously become elevated from normal values that are <0,01 (or <10 if expressed as picomolar/nanomolar). The increase of both the 5-HTOL level and the 5-HTOL/5-HIAA ratio persist for several hours after alcohol has disappeared from the body. These findings have made 5-HTOL and the 5-HTOL/5-HIAA ratio markers of recent alcohol consumption in the treatment of alcohol dependence and in forensic medicine, e.g. during post-mortem body examination. The preference has been for measuring the ratio because 5-HTOL levels, but not the ratio, are increased also after ingestion of food rich in serotonin, and because the range for normal and abnormal 5-HTOL levels, but not the ratios, are overlapping. As an alternative also the ratio between urinary 5-HTOL and other urinary excretion products, such as creatinine, have been used.

The term "15-HTOL" includes 5-HTOL compounds, such as free 5-HTOL, its glucuronide (tryptophol-5-gucuronide, T-5-G) and its sulphate, if not otherwise specified.

Increased levels of 5-HTOL compounds after alcohol consumption have so far been detected in urine, plasma, cerebrospinal fluid (CSF). It is most likely that one can detect 5-HTOL compounds also in serum, tear fluid, sweat, saliva etc. The normal level of 5-HTOL compounds and the balance between free 5-HTOL and its conjugated forms may be different between various types of sample samples.

Compared to 5-HIAA, 5-HTOL is complicated to measure. It occurs in lower concentrations than 5-HIAA and the conjugated forms are in excess with a strong predominance for the glucuronide. The presently used method for measuring 5-HTOL is gas chromatography in combination with mass spectrometry (GC/MS), a method requiring expensive instruments. A high pressure liquid chromatography (HPLC) method has been developed but it suffers from the drawback that of "false peaks", i.e. overlapping $R_f$ for 5-HTOL and other compounds. Both methods require that the glucuronide (T-5-G) has to be converted enzymatically to free 5-HTOL before the assay. Thus there is a need for a cheap, simple and reliable method for measuring 5-HTOL compounds in various body fluids.

For earlier published articles within the field of the invention see separate list at the end of the descriptive part.

Reference may also be made to Dabadie et al, Synapse 14: 178–183 (1993), Iijima et al, Acta histochem 89: 141–156 (1990), U.S. Pat. No. 4,762,781 (Geffard) and EP-A-216162 (A/S De Danske Sukkerfabrikker)

OBJECTIVES OF THE PRESENT INVENTION

The primary objective of the invention is to provide an immunoassay method for the measurement of a 5-HTOL compound in samples containing free 5-HTOL together with its conjugates without prior hydrolysis of endogenous 5-HTOL conjugates.

An second objective is to provide an antibody allowing for an immunoassay of a 5-HTOL compound.

A third objective is to provide derivatives of T-5-G that may be used as immunogens or as 5-HTOL analogues mimicking the structure of corresponding native 5-HTOL compound in various assays, e.g. competitive immunoassays for 5-HTOL compounds.

The Discovery Behind the Invention

The invention is based on our discovery that one can obtain antibodies that bind to a 5-HTOL compound by raising a humoral immune response in the appropriate animals using an immunogenic form of the β-glucuronide of 5-HTOL and D-glucopyranosiduronic acid (i.e. an immunogenic form of 3-(2-hydroxyethyl)indole-5-O-β-D-glucopyranosiduronic acid) as the immunogen.

The Inventive Antibody Preparation

The first aspect is thus an antibody specific against a 5-HTOL compound. By the term "specific" is meant that the antibody during immunoassay conditions preferentially will bind to a 5-HTOL compound with no disturbing binding activity against other endogenous substances in human samples, for instance serotonin (5-HT), 5-HIAA or other structurally related substances, such as other indoles or glucuronides. In the presently preferred mode the inventive antibody preparation preferentially binds to T-5-G compared to other endogenous 5-HTOL compounds. The antibody preparation has an acceptable low binding activity to potential disturbing substances, such as other indoles and glucuronides, that may be present in body fluids. See the experimental part. Since the levels of free 5-HTOL, T-5-G and sulphated 5-HTOL all are elevated as a consequence of recent alcohol intake, useful antibodies may react with one, two or all of these 5-HTOL compounds.

The term antibody encompasses various antibody preparations having the above-mentioned specificity, such as the intact antibody and various active fragments (antigen/hapten binding fragments), such as Fab, Fab', Fv, F(ab')$_2$ etc. It also covers derivatized antibodies, such as antibodies to which labels have been attached covalently, such as biotin, hapten, enzymes, enzyme substrates, cofactors, fluorophors, chemiluminescers, chromophors, radioactive isotopes, metals, particles etc, and carrier molecules, such as insoluble and soluble polymers.

The inventive antibody may be a polyclonal or monoclonal preparation. It may contain a mixture of a definite number of monoclonals. It can be obtained by commonly known methods, except that our novel T-5-G derivatives (conjugates) should be used, for instance as an immunogen to raise polyclonal antibodies or as an antigen for the screening of immune response or of cell lines (e.g. hybridomas) secreting the inventive antibody or various antibody libraries from which each individual antibody component can be isolated together with the corresponding coding sequence. Thus the techniques contemplated do also encompass antibodies obtained via selection by phage display techniques. Once obtained, the inventive antibody preparation may be modified by recombinant techniques.

The best mode at the priority date for obtaining the inventive antibody preparation is given in the experimental section and utilizes as the immunogen the conjugate between keyhole limpet hemocyanine (KLH) with T-5-G as defined in patent example 3 (reaction scheme 2) and selection of appropriate hybridoma clones as described in the experimental section. The best mode inventive antibody thus preferentially binds to T-5-G among various 5-HTOL compounds present in native samples.

The Inventive 5-HTOL Analogues

The T-5-G (i.e. 3-(2-hydroxyethyl)indole-5-O-β-D-glucopyranosiduronic acid) and its derivatives are novel in the sense that they never have been isolated before. Thus the broadest concept of this aspect of the invention is a 5-HTOL compound characterized in exhibiting the structure of 3-(2-hydroxyethyl)indole-5-O-β-D-glucopyranosiduronic acid, optionally derivatized at one or more OH in the carbohydrate part, i.e. at an alcoholic hydroxy group (positions 2, 3 and 4) or at the carboxy group (position 6) or at the 3-hydroxyethyl hydroxyl or at the indole nitrogen.

Derivatization at an alcoholic hydroxy group may be accomplished as normally is done for glucuronide derivatives, e.g. selective alkylation or acylation at positions 2, 3 and/or 4, either before or after glucuronide formation with free 5-HTOL. Derivatization at the carboxy group of the glucuronide or of the free glucuronic acid may lead to amides and esters in which the carboxy group is further derivatized. See the experimental part.

T-5-G is preferably derivatized at the carboxy group to contain a covalently bound carrier molecule, preferably of polymeric nature, for instance an immunogenic protein carrier, such as human or bovine serum albumin, KLH or the like, or an insoluble or insolubilizable carrier polymer (support) of the type used as separation media in chromatography and immunoassays (e.g. supports made from synthetic polymers, such as polystyrene, or from polysaccharide, such as agarose, dextran, cellulose, starch and the like).

The derivatization of the T-5-G structure may also be made in order to introduce a covalently attached analytically detectable group, preferably via the carboxy group. The analytically detectable group may be of the same type as discussed for the inventive antibodies, see above.

The preferred methods of synthesizing the inventive T-5-G compounds at the priority date are apparent from the experimental part.

The Inventive Immunoassay Aspect

This aspect of the invention encompasses contacting a sample containing a 5-HTOL compound with the inventive antibody under conditions allowing formation of an immune complex comprising both a 5-HTOL compound and the inventive antibody. The conditions are then selected so that the amount of complex formed will be a measure of the amount of the 5-HTOL compound in the sample.

Determination of the complex is carried out according to methods well-known in the art, for instance either as the complex as such or as the decrease in the amount of uncomplexed inventive antibody added.

One general type of immunoassay that can be employed utilizes a labelled immune reactant that is able to form immune complexes in an amount that is related to the amount of the 5-HTOL compound present in the sample. In principle the label may be of the same general types as indicated above for 5-HTOL glucuronide analogues and antibodies.

Immunoassays utilizing labels are often divided into heterogeneous and homogeneous assays. The homogeneous variants utilize no separation step of complex-bound labelled reactant from uncomplexed labelled reactant. This makes it imperative to use a label that change its signal as a consequence of complex formation. In heterogeneous assay variants the labelled reactant that is bound in an immune complex is physically separated from the labelled reactant not bound in the complex. The heterogeneous variants thus have no demand for labels changing their signal due to complex formation, meaning that also radioactive isotope labels can be used.

Still another way of dividing immunoassays are in competitive and non-competitive (sandwich) variants. In the former case the 5-HTOL compound binding to the inventive antibody and present in the sample is allowed to compete with a T-5-G analogue for a limited amount of the inventive antibodies (the 5-HTOL compound reactive with the antibody plus the T-5-G analogue), whereafter the amount of complex between the T-5-G analogue and the inventive antibody is determined and related to the amount of the 5-HTOL compound in the sample. The T-5-G analogue is in this case preferably a labelled or a carrier bound T-5-G derivative as defined above. In case the T-5-G analogue is the labelled reactant, the inventive anti-5-HTOL antibody used may be in insolubilized form (for instance linked to a support) or soluble form. An alternative is a variant in which an insoluble T-5-G analogue is competing with a 5-HTOL compound of the sample for a limited amount of the soluble inventive anti-5-HTOL antibody.

The preferred immunoassay variants at the priority date encompass heterogeneous competitive immunoassays as described above. See also the experimental part.

Among assay variants utilizing no labelled reactant may be mentioned biosensor techniques where binding between antigen/hapten and antibodies is occurring at a surface.

The sample may be serum, plasma, urine, CSF or any other sample that may contain one or more 5-HTOL compounds.

The temperature and pH-conditions that are normal for immunoassays are applicable, i.e. 0–40° C., with preference for 15–35° C., and pH 4–9, with preference for pH 5–8.

The result of the inventive immunoassays may be used in diagnostic methods for determining recent alcohol consumption of an individual in the same way as done earlier for 5-HTOL compounds (see the introductory part). This means that in the preferred variants of the inventive diagnostic methods found levels of 5-HTOL compounds may be put into relation with some other compound, e.g. the levels of 5-HIAA or creatinine. For immune assays the amount of immune complex formed or any other measure of the amount of 5-HTOL compounds in the sample may of course be directly related to recent alcohol consumption equally well as the level a 5-HTOL compound as such. The diagnostic method is particularly well adapted to human individuals.

EXPERIMENTAL PART

Synthesis

Example 1

Synthesis and Purification of 3-(2-hydroxyethyl) indole-5-yl-O-β-D-glucopyranosiduronic Acid (I)

(FIG. 1): 2-(5-Hydroxy-3-indolyl)ethyl alcohol (151 mg), $MgCl_2$ (50 mg), uridine 5'-diphosphoglucuronic acid triammonium salt (490 mg), uridine 5'-diphosphoglucuronyl transferase (182 mg) (Type III from bovine liver, Sigma) and 40 ml of 0.1 M pH 7.4 Tris-buffer were added to a 200 ml E-flask. The flask was sealed with parafilm and incubated in a shaker-incubator at 37° C. and 150 rpm. Small samples were extracted from the incubation at different timepoints, and analysed after cooling, centrifugation, filtration and acidification by analytical PepRPC on a FPLC system, in order to follow the reaction. The concentration of 3-(2-hydroxyethyl)indole-5-yl-O-β-D-glucopyranosiduronic acid (I) reached plateau-levels after 20 h and remained at that level for more than 7 h.

The incubation was stopped on ice for 15 min followed by centrifugation at 10000 rpm at 5° C. for 30 min using a JA-10 rotor in a J2-21 M/E Beckman centrifuge. The supernatant was then filtered through cotton wool, acidified to below pH 3 by adding HCl. Methanol was added to a final concentration of 2.5%. Of this mixture 1/3 at a time was purified on a Pep RPC HR 16/10 column in a water/methanol system. The column was first extensively equilibrated in water. The sample was applied in 2.5% methanol and a gradient of 2.5 to 5.5% methanol was run for 85 min and then isocratic for 60 min and thereafter a gradient of 5.5 to 50% methanol for 100 min. The flow speed was all the time 3.5 ml/min. 3-(2-Hydroxyethyl)indole-5-yl-O-β-D-glucopyranosiduronic acid (I) was eluted at 5.5% methanol. Pooling of fractions and purity of the preparations was monitored by TLC (n-butanol:acetic acid:ethyl acetate:water, 1:1:1:1). The yield after purification was 65 mg. $^1$NMR (D$_2$) δ3.5(t 2H), 3.7–3.79(m 3H), 3.93(t 2H), 4.16(d 1H), 5.19(d 1H), 7.12(q 1H), 7.33(s 1H), 7.44(d 1H), 7.45(d 1H). J$_{1,2}$ for H in glucopyranosiduronic acid was 7.8 cps indicating a β form. $^{13}$CNMR(D$_2$O) 27, 61, 71, 72, 74, 75, 102, 106, 111, 112, 113, 125, 127, 133, 150, 172. The pattern of the carbon peaks of the glucopyranosiduronic acid agrees with the β form.

Example 2

Synthesis of N-(2-pyridyldithioethyl)-(2-hydroxyethyl)indole-5-yl-O-β-D-glucopyranosiduronic Acid (II)

Figure 2:
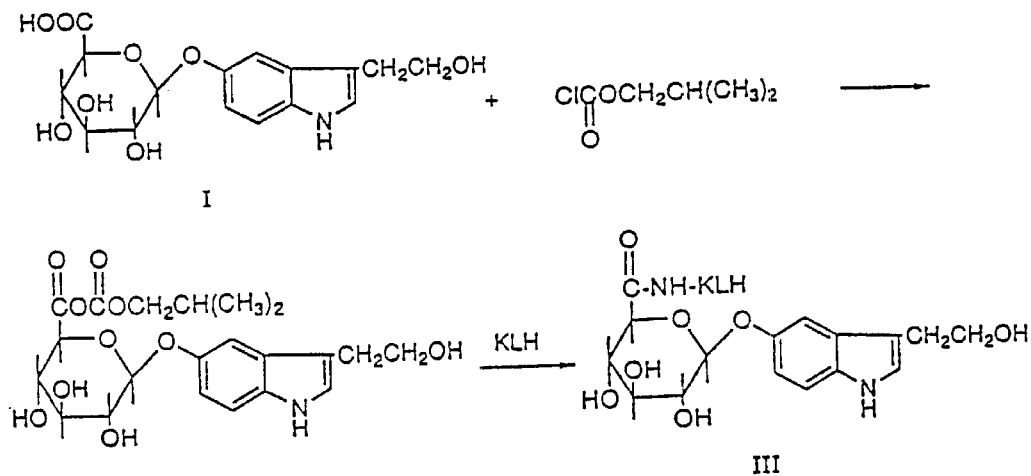

FIG. 2. 3-(2-Hydroxyethyl)indole-5-yl-O-β-D-glucopyranosiduronic acid (I) (52 mg, 0.153 mmole) was dissolved in ~1 ml DMF (dried with molecular sieves) in 5 ml reacti vial. Thereafter O-(N-succinimidyl)-N,N,N',N'-tetramethyluronium tetrafluoroborate (TSTU)(73 mg, 0.243 mmole) and diisopropylethylamine (84 μl, 0.456 mmole) were added. The reaction was run for 35 min in room temperature.

Cysteamine-2-pyridyldisulfide hydrochloride (72 mg, 0.324 mmole) was added to another reacti vial followed by DMF (0.5 ml) and diisopropylethylamine (56 μl, 0.324 mmole). To this solution the hydroxysuccinimidyl activated acid (I) was added. The reaction was run for 1 h and then evaporated in vacuum at low pressure giving an oil. TLC (n-butanol:ethyl acetate:acetic acid:water=1:1:1:1) showed that almost all (I) had reacted. The oil was dissolved in 3 ml of 27% methanol, divided in three portions and fractionated on a PepRPC column HR 16/10 using a gradient of 25–60% methanol containing 0.2% acetic acid with a flow rate of 3.5 ml/min. The desired product (II) was eluted at a gradient of 43% methanol containing 0.2% acetic acid. Fractions with (II) were pooled and concentrated by evaporation in vacuum and finally freeze dried giving 26 mg of (II) as a white powder. $^1$HNMR(D$_2$O) δ2.98(t 2H), 3.01–3.12(m 2H), 3.54–3.63(m 2H), 3.71–3.77(m 3H), 3.87(t 2H), 3.97–4.01(m 1H), 5.22(d 1H), 7.14–7.17(m 2H), 7.24(s 1H), 7.42(t 1H), 7.47(t 1H), 7.48(s 2H), 8.3(d 1H).

Example 3

Synthesis of the KLH Conjugate (III) (FIG. 2)

Keyhole limpet hemocyanine (KLH)(73.5 mg) was dissolved in 6.5 ml of 0.1 M borate buffer keeping pH 9.5. Undissolved substance was removed by filtration and the protein content of the solution was analysed by amino acid analysis to be 37 mg/ml protein. To this ice-cold solution of KLH 0.8 ml of a solution of a mixed anhydride of 3-(2-hydroxyethyl)indole-5-yl-O-β-D-glucopyranosiduronic acid (0.025 mmole) was added. The latter compound was prepared by dissolving 3-(2-hydroxyethyl)indole-5-yl-O-β-D-glucopyranosiduronic acid (I) (10.6 mg, 0.0312 mmole) in 1 ml of tetrahydrofuran in a 5 ml reacti vial. Nitrogen gas was let into the vial and the latter was placed in an ice-bath. After 15 min isobutylchloroformiate (4.1 μl, 0.0312 mmole) and triethylamine (4.3 μl, 0.0312) were added and the reaction the acid (I) and isobutyl chloroformiate was completed in 30 min at 0° C. The reaction between KLH and the anhydride was run at 20 min at a 0° C. and then placed in a refrigerator over night. The tetrahydrofuran was removed in a vacuum evaporator and the reaction solution (4.8 ml) was separated on two Sephadex G25 M PD-10 columns which were equilibrated with 2 mM phosphate buffer pH 7.5. The conjugate was eluted with 3.2 ml buffer. The total volume was 6.4 ml. The protein content was determined with amino acid analysis to be 3.04 mg/ml. The degree of substitution was determined with UV-spectroscopy to be 270 compound I per KLH (calc. on Mw. 3 000 000).

Example 4

Figure 3:
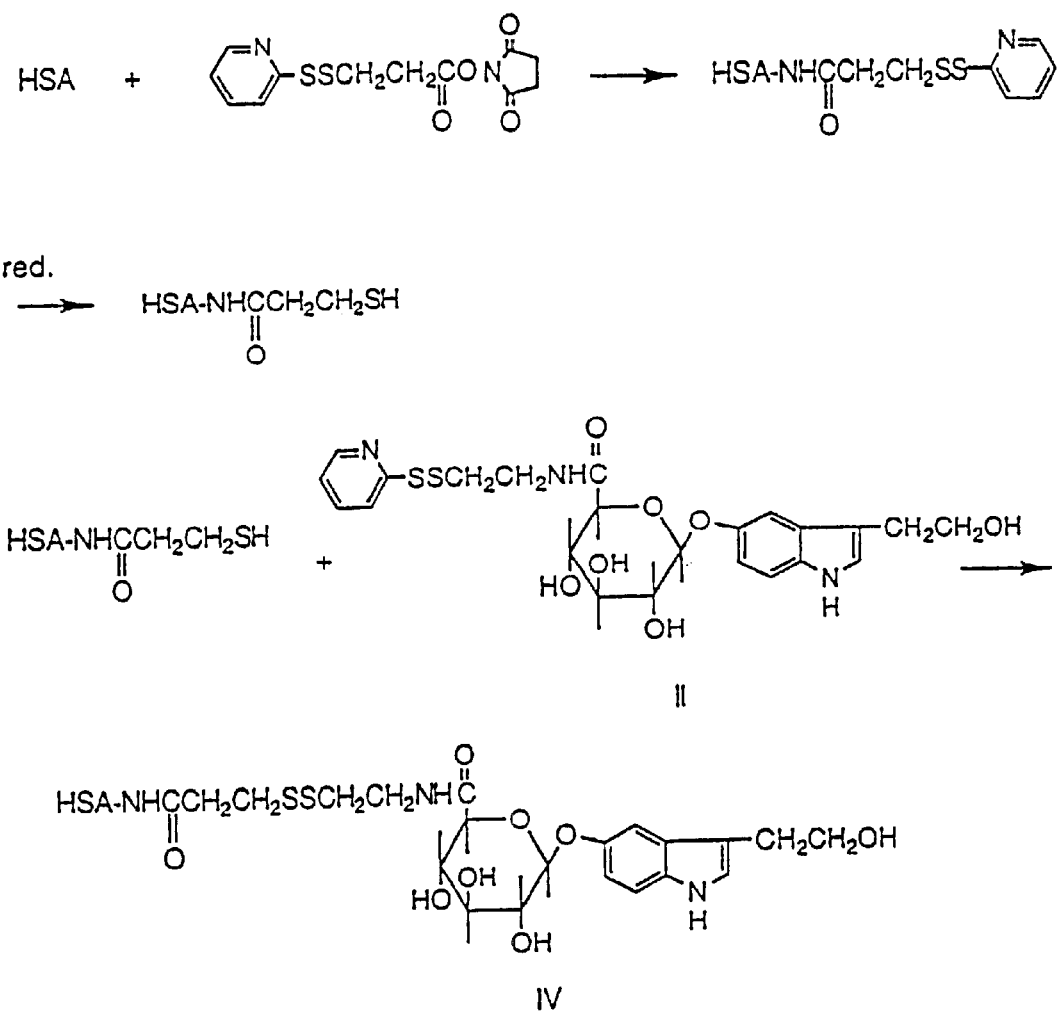

Synthesis of HSA Conjugate (IV) FIG. 3

Human serum albumin (HSA) (28.5 mg, 0.425 μmole) was dissolved in 1.73 ml of 0.2 M phosphate buffer keeping pH 8.5. To this solution N-succinimidyl 3-(2-pyridyldithio)propionate (SPDP) (2.0 mg, 6.38 μmole) in 0.178 ml ethanol was added. The reaction was run for 15 min and then the pH was adjusted to 4.35 with conc and 2 M acetic acid. Dithiotreitol (5.7 mg) was added to reduce the disulfide bond. The reaction was run for 10 min and then the reaction solution was desalted on a Sephadex G25 M PD-10 column. The protein was eluted with 2.4 ml of 5 mM phosphate buffer keeping pH 4.5 and containing 0.3 M sodium chloride. The HSA conjugate was analysed to contain 6.7 SH/HSA and the protein content was 1.0.34 mg/ml.

To this HSA conjugate solution (2.48 μmole SH groups) N-2-pyridyldithioethyl) 3-(2-hydroxyethyl)indole-5-yl-O-β-D-glucopyranosiduronamide (II) (1.9 mg, 3.72 μmole) dissolved in 0.216 ml of acetonitril was added. The pH was adjusted to 8.45. The reaction was run for 24 h at room temperature and then fractionated on two Sephadex G25 M PD-10 columns equilibrated with 50 mM phosphate buffer pH 7.4. The conjugate was eluted with 3.9 ml buffer.

Example 5

I$^{125}$-Labelling of HSA-conjugate IV

Labelling with I$^{125}$ was carried out with the Chloramine-T method (Greenwood F. C. et al., Biochem. J. 89 (1963) 114–123).
Antibodies
Immunogens
Type 1: Obtained by reducing compound II with NaHB$_4$ and then reacting the reduced derivative with [17-((iodoacetyl)

amino)-3,6,9,12,12-pentaoxaheptadacanoyl]amino-KLH or [17-((iodoacetyl)amino)-3,6,9,12,12-pentaoxaheptadacanoyl]amino-HSA (Åkerblom et al., Bioconjugate Chemistry 4 (1993) 455–466) to give Conjugate A and B, respectively.

Type 2: Conjugate C is the HSA conjugate IV.

Type 3: Conjugate D and conjugate E correspond to conjugate III with KLH (270 T-5-G per mol KLH) and HSA (2.5 groups of T-5-G per mole HSA), respectively.

Immunizations

Type 1: Five Balb/c mice were primed with 50 μg immunogen (conjugate A) in Freunds' complete adjuvant (FCA). Subsequent injections were given every four weeks without adjuvant (4×50 μg).

Type 2: Two Balb/c mice were primed with 25 μg immunogen (conjugate C) in Freunds' complete adjuvant (FCA) and boosted every four weeks without adjuvant (4×50 μg).

Type 3: Three groups of three Balb/c mice in each group were primed with 50 μg immunogen (conjugate D) in FCA and boosted after four weeks without adjuvant 50 μg and after four additional week with 50 μg of conjugate D.

Immune response: This was tested by ELISA (see below) and inhibition-ELISA (se below, specificity). All of the sixteen mice gave a high titre in the ELISA, but it was only possible to inhibit the binding to the T-5-G derivative coated on the walls of the microtitre wells with T-5-G for four mice (all immunized according to Type 3). These four mice were boosted (3×25 μg) day one, day two and day three and fused day four.

Fusions

The fusions were performed by the aid of polyethylene glycol (PEG) and with SP2/0 myeloma cells as a fusion partner. The cell suspension was seeded in 96 wells microtiter plates and cultured in Dulbecco's Modified Eagles Medium (DMEM) supplemented with 15% fetal calf serum and selected with HAT (hypoxanthine-aminopterin-thymidine). Peritoneal macrophages were used as feeder cells. The supernatants were screened by ELISA (see below). Positive hybridomas were tested in inhibition-ELISA (see below) with T-5-G as an inhibitor. The four fusions resulted in 37 hybridomas and based on the results of the inhibition-ELISA twelve of them were chosen for cloning.

Cloning and Screening

Cloning: 0.8 cells/well were seeded in 96-well plates with peritoneal macrophages as feeder cells. Wells with one cell were observed on day five and tested in the same way as the hybridomas and in inhibition-ELISA on day seven.

ELISA: The wells of 96-wells ELISA microtiter plates were coated with conjugate B for type 1 immunizations, and with conjugate E for type 2 and 3 immunizations in 0.1 M Na-carbonate pH 9.5 overnight at room temperature, then washed 3 times with 0.9% NaCl containing 0.02% Tween® 20. Culture supernatants diluted 1:5 in $Ca^{2+}/Mg^{2+}$ free PBS containing 0.05% Tween 20 were then added and the plates were incubated for 2 h at 37° C. The plates were again washed as described above. Antibody binding was detected with rabbit Fab' anti-mouse IgFc-β-galactosidase conjugate and o-nitro-phenyl-β-galactoside as the enzyme substrate with 30 min substrate incubation.

Inhibition-ELISA: This was performed as described for ELISA except that the culture supernatants were incubated with T-5-G (1 μg/well) before being added to the wells.

Results: Six clones produced antibodies that in inhibition experiments were shown to be reactive against T-5-G. One of these was then further studied in crossreactivity.

Cross Reactivities

Crossreactivity for various substances was measured in the immunoassay method described below with dilutions (in the diluent) of the tested substance used in stead of urine or standard. The concentration range tested for each substance covered three magnitudes and was up to or above one magnitude the highest noted literature value.

The tolerance limit for disturbing binding activities of other substances is measured as inhibition of the reaction between the protein conjugate IV and the inventive antibody (cross reactivity) and is given in relation to the concentration of T-5-G at the detection limit. Acceptable inhibition limits for various substances in urine are apparent from Table 1 for a 50 nM detection limit of T-5-G.

TABLE 1

Urine. Potentially disturbing substances, their highest concentrations and allowable maximal cross reactivity.

| Highest urine conc μM | Acceptable Crossreactivity | Potentially disturbing substance |
| --- | --- | --- |
| 70 | 0.07% | 5-HIAA |
| 8 | 0.6% | tryptophan |
| 0.8 | 6% | tryptamine |
| 0.7 | 7% | serotonin |
| 0.1 | 50% | melatonin |
| 70 | 0.07% | indolyl acetic acid |
| 3000 | 0.002% | indoxyl sulphate |
| 50[1] | 0.1% | 5-hydroxytryptophan |
| 100[1] | 0.002% | indoxyl-β-D-glucuronide |
| 100[1] | 0.002% | p-nitrophenyl-β-D-glucuronide |
| 0.1[1] | 50% | testosterone-β-D-glucuronide |
| 0.1[1] | 50% | estrone-β-D-glucuronide |
| 100[1] | 0.05% | indole-3-aldehyde |
| 1[1] | 5% | 5-methoxytryptophol |
| 1 | 5% | 5-methoxytryptamine |

[1]Estimated level

The antibody tested for crossreactivity complied with the criteria set forth in table 1.

Immunoassay

Materials: 3-(2-hydroxyethyl)indole-5-O-β-D-glucopyranosiduronic acid, $^{125}$I-labelled T-5-G-HSA conjugate (conjugate IV, Scheme 3) and mouse monoclonal anti-5-HTOL antibody raised against a T-5-G-KLH conjugate (conjugate III, Scheme 2) were all as described above. Diluent was 0.05 M sodium phosphate buffer, pH 7.0, containing 0.01 M EDTA, 0.1% Tween® and 1% BSA. Decanting solution was Pharmacia decanting suspension without added antibody suspension (Pharmacia Diagnostics AB). μ-agarose particles carried covalently bound sheep-anti-mouse antibody.

Assay Principle: Competition between sample T-5-G and labelled conjugate IV for a limited amount of mouse anti-5-HTOL antibody with subsequent precipitation by addition of sheep-anti-mouse antibody bound to agarose μ-particles.

Assay Procedure: Pipette to a test tube 50 μl urine or standard, 50 μl tracer solution, 50 μl antibody solution (one of the above-mentioned six selected clones, 5 μg/ml), mix on shaker ~600 rpm for ~1 min, allow to stand for 1.5 h at room temperature, 50 μl of the sheep anti-mouse micro-agarose suspension (~100 mg/ml), mix as above and let stand for another 0.5 h, then add 2 ml decanting solution, centrifuge 10 min at 3000 rpm, with tubes in Pharmacia decanting racks, in the JR-3.2 Rack Rotor, in a Beckman J-6B centrifuge. Within 5 min after completed centrifugation decant the supernatant and let tube racks stand inverted on absorbtive tissue for 2 min. Finally the remaining radioactivity in the tubes is measured in a gamma counter. A standard curve is made with T-5-G in the diluent at 10, 100, 1000 and 10000 nmol/L.

As an example results from a test with voluntary self reports of alcohol consumption morning after urine is shown in Table 2A. Urine samples were kept frozen at −70° C. until use, after thawing the samples were briefly centrifuged before analysis, all samples were analysed in duplicates. Creatinine analysis was done according to Jaffé.

TABLE 2A

Alcohol intake versus the ratio nm GHTO/nm creatinine in urine. Males.

| g EtOH/kg body weight | nM T-5-G/nM creatinine | g EtOH/kg body weight | nM T-5-G/nM creatinine |
|---|---|---|---|
| 0.00 | 9.39 | 1.00 | 193.47 |
| 0.00 | 17.22 | 1.06 | 189.19 |
| 0.06 | 7.26 | 1.08 | 80.93 |
| 0.12 | 6.11 | 1.20 | 104.90 |
| 0.13 | 10.61 | 1.24 | 435.24 |
| 0.14 | 16.27 | 1.25 | 35.76 |
| 0.17 | 13.25 | 1.37 | 419.17 |
| 0.26 | 11.78 | 1.40 | 524.64 |
| 0.68 | 160.30 | 1.47 | 309.99 |
| 0.76 | 221.51 | 1.48 | 50.64 |
| 0.90 | 522.56 | 1.68 | 262.03 |
| 0.95 | 77.56 | 1.79 | 486.07 |
| 0.96 | 77.20 | 1.83 | 495.79 |
|  |  | 1.96 | 492.83 |

REFERENCES

Inventors' Publications

1. Beck et al., Levels of 5-hydroxytryptophol in cerebrospinal fluid from alcoholics determined by gas chromatography-mass spectrometry. Biochem. Pharmacol. 29 (1980) 693–696.
2. Beck et al., Concentration of serotonin metabolites in the cerebrospinal fluid from alcoholics before and during disulfiram therapy. Acta Pharmacol. Toxicol. 47 (1980) 305–307.
3. Beck et al., 5-hydroxytryptophol in the cerebrospinal fluid and urine of alcoholics and healthy subjects. Naunyn-Schmiedeberg's Archives of Pharmacology 321 (1982) 293–297.
4. Beck et al., 5-hydroxyindoleacetic acid and 5-hydroxytryptophol levels in rat brain: effects of ethanol, pyrazole, cyanamide and disulfiram treatment. Drug and Alcohol Dependence 16 (1986) 303–308.
5. Helander et al., Effects of ethanol, acetaldehyde and disulfiram on the metabolism of biogenic aldehydes in isolated human blood cells and platelets. Biochem. Pharmacol. 36 (1987) 3981–3985.
6. Helander et al., Determination of urinary 5-hydroxyindole-3-acetic acid by high-performance liquid chromatography with electro detection and direct sample injection. Anal. Biochem. 196 (1991) 170–173.
7. Borg et al., Carbohydrate deficient transferrin and 5-hydroxytryptophol: two new markers of high alcohol consumption. In: Measuring Alcohol Consumption (Eds. Litten et al), 149–159 (1992) Humana Press Inc, Clifton, N.J.
8. Helander et al., Urinary excretion of 5-hydroxyindole-3-acetic acid and 5-hydroxytryptophol after oral loading with serotonin. Life Sciences 50 (1992) 1207–1213.
9. Helander et al., Determination of elevated 5-hydroxytryptophol levels in urine using high-performance liquid chromatography with electrochemical detection. J. Chrom. Biomed. Appl. 579 (1992) 340–345.
10. Helander et al., Urinary 5HTOL/5HIAA as biochemical marker of postmortem ethanol synthesis (Letter). Lancet 340 (1992) 1159.
11. Voltaire et al., Urinary 5-hydroxytryptophol: a possible marker of recent alcohol consumption. Alcoholism: Clin. Exp. Res. 16 (1992) 281–285.
12. Helander et al., Time course of ethanol-induced changes in serotonin metabolism. Life Sciences 53 (1993) 847–855.
13. Voltaire-Carlsson et al., Detection of relapses in alcohol-dependent patients: comparison of carbohydrate-deficient transferrin in serum, 5-hydroxytryptophol in urine, and self-reports. Alcoholism: Clin. Exp. Res. 17 (1993) 703–708.
14. Helander et al., Influence of genetic variation in alcohol and aldehyde dehydrogenase on serotonin metabolism. Life Sciences 55 (1994) 359–366.
15. Helander et al., The use of 5-hydroxytryptophol as an alcohol intake marker. Alcohol & Alcoholism 2 (suppl) (1994) 497–502.
16. Beck et al., Changes in serotonin metabolism during treatment with the aldehyde dehydrogenase inhibitors disulfiram and cyanamide. Pharmacol. Toxicol. 77 (1995) 323–326.
17. Borg et al., New markers of alcohol consumption: CDT and 5HTOL. Advances in Neuroscience (Proceedings of the IX World Congress of Psychiatry) (Ed. Beigel) 1:3–7 (1995).
18. Borg et al., Detection of relapses in alcohol dependent patients using carbohydrate-deficient transferrin: improvement with individual reference levels during long-term monitoring. Alcoholism: Clin. Exp. Res. 19 (1995) 961–963.
19. Helander et al., Distinguishing ingested ethanol from microbial formation by analyzing urinary 5-hydroxytryptophol and 5-hydroxyindole acetic acid. J. For. Sci. 40 (1995) 95–98.
20. Helander et al., 5-hydroxytryptophol conjugation in man: influence of alcohol consumption and altered serotonin turnover. Life Sciences 56 (1995) 1529–1534.
21. Helander et al., Determination of 5-hydroxytryptophol in urine by high-performance liquid chromatography: application of a new post-column derivatization method with fluorometric detection. J. Pharmaceut. Biomed. Anal. 13 (1995) 651–654.
22. Helander et al., Longitudal comparison of carbohydrate-deficient transferrin and γ-glutamyltransferase: complementary markers of excessive alcohol consumption. Alcohol & Alcoholism 31 (1996) 101–107.
23. Jones et al., Disclosing recent drinking after alcohol has been cleared from the body (Letter). J. Anal. Toxicol. 20 (1996) 141–142.
24. Helander et al., Laboratory testing for recent alcohol consumption: comparison of ethanol, methanol, and 5-hydroxytryptophol. Clin. Chem. 42 (1996) in press.

Publications Potential Interest

25. Feldstein et al., Biogenic amines, biogenic aldehydes, and alcohol. Quarterly Journal on Studies on Alcohol. 25 (1964) 218–225.
26. Davis et al., The alteration of serotonin metabolism to 5-hydroxytryptophol by ethanol ingestion in man. J. Lab. Clin. Med. 69 (1967) 132–140.
27. Feldstein et al., 5-hydroxytryptamine metabolism in rat brain and liver homogenates. Br. J. Pharmacol. 34 (1968) 38–42.
28. Yoshimoto et al., Occurrence in vivo of 5-hydroxytryptophol in the brain of rats treated with ethanol. Alcohol & Alcoholism 27 (1992) 131–136.

Review Articles

29. Rosman et al., Diagnostic utility of laboratory tests in alcoholic liver disease. Clin. Chem. 40 (1994) 1641–1651.
30. Conigrave et al., Diagnostic tests for alcohol consumption. Alcohol & Alcoholism 30 (1995) 13–26.
31. O'Neal et al., Postmortem production of ethanol and factors that influence interpretation. Am. J. For. Med. Path. 17 (1996) 8–20.

What is claimed is:

1. An antibody specific for a 5-HTOL compound wherein said 5-HTOL compound is selected from the group consisting of 5-hydroxytryptophol, a glucuronide conjugate of 5-hydroxytryptophol, and a sulphate conjugate of 5-hydroxytryptophol.

2. The antibody of claim 1 wherein said antibody has no specific binding activity against an endogenous substance other than a 5-HTOL compound in a human sample to be assayed.

3. The antibody of claim 2 wherein said endogenous substance includes serotonin (5-HT), 5-HIAA, and structurally related indoles and other glucuronides.

* * * * *